United States Patent [19]

Alburger

[11] 3,978,717

[45] Sept. 7, 1976

[54] INHIBITED PRE-WASH STRIPPER COMPOSITION FOR WATER-WASHABLE INSPECTION PENETRANTS

[76] Inventor: James R. Alburger, 5007 Hillard Ave., La Canada, Calif. 91011

[22] Filed: Jan. 13, 1975

[21] Appl. No.: 540,418

[52] U.S. Cl. .............................. 73/104; 23/230 R; 252/301.19; 252/408
[51] Int. Cl.² .................. G01N 19/08; G01N 31/22
[58] Field of Search .......... 252/408, 301 P; 73/104; 23/230 R

[56] References Cited
UNITED STATES PATENTS

| | | | |
|---|---|---|---|
| 3,429,826 | 2/1969 | Alburger | 252/408 |
| 3,433,062 | 3/1969 | McLina | 252/408 |
| 3,436,959 | 4/1969 | Redemann | 252/408 |
| 3,489,898 | 1/1970 | Alburger | 252/408 |
| 3,607,784 | 9/1971 | Fijalkowski | 252/408 |
| 3,636,759 | 1/1972 | Alburger | 252/408 |

OTHER PUBLICATIONS
Lange: *Handbook of Chemistry* McGraw–Hill (1961) pp. 444–445.

*Primary Examiner*—Benjamin R. Padgett
*Assistant Examiner*—David Leland

[57] ABSTRACT

A pre-wash stripper composition for use in the water-washable inspection penetrant process consisting of water saturated with dissolved penetrant. The saturated solution cannot dissolve more penetrant, and is therefore incapable of causing depletion of crack entrapments, but when applied to test surfaces by spray, it is capable of removing surface penetrant from test parts to completion of the so-called incubation of washing, and for purposes of recovery of excess surface penetrant for re-use. Test parts which have been pre-washed with the inhibited saturated solution may be finish-washed in clean water with a minimum amount of penetrant carry-over into the finish-wash water.

2 Claims, No Drawings

3,978,717

INHIBITED PRE-WASH STRIPPER COMPOSITION FOR WATER-WASHABLE INSPECTION PENETRANTS

RELATED PATENT APPLICATIONS

Application Ser. No. 431,236, filed Jan. 7, 1974, for "WATER-WASHABLE INSPECTION PENETRANT EMPLOYING MINERAL SOLVENT AND A FATTY ACID SOLUBILITY PROMOTER", now U.S. Pat. No. 3,930,407.

Application Ser. No. 482,465, filed June 24, 1974, for "ENHANCED STABILITY WATER-WASHABLE PENETRANT COMPOSITION AND PROCESS", C.I.P. of Ser. No. 327,306, filed Jan. 29, 1973, Same Title, now U.S. Pat. No. 3,896,664.

Application Ser. No. 513,084, filed Oct. 8, 1974, for "WATER-WASHABLE INSPECTION PENETRANT EMPLOYING TRIGLYCERIDES AND POLYGLYCERIDES OF FATTY ACIDS", now U.S. Patent No. 3,929,664.

This invention relates to water-washable inspection penetrant processes. More particlarly, the invention relates to a pre-wash composition which may be used to remove excess surface penetrant from test parts without depleting entrapments of penetrant in surface discontinuities.

The water-washable inspection penetrant process is used extensively for nondestructive testing and inspection of critical aircraft parts. Various kinds of penetrants have been utilized in the past, some being formulated on water-soluble liquids such as glycols, others being formulated on self-emulsifiable liquids such as oils containing detergents and solvent couplers which cause emulsions to form upon contact with water. Still others are formulated on the "slow-solubility" liquids such as are disclosed and claimed in my copending application Ser. Nos. 431,236, 482,465, and 513,084.

Regardless of the chemical formulation which is used, the inspection penetrant always contains an indicator dye, either visible-color, fluorescent, or both, depending on the desired mode of usage. In use, the dyed liquid penetrant is applied to test parts, the parts are washed in water to remove surface penetrant, and then the parts are dried and inspected for visible-color or fluorescent indications of penetrant entrapments which may remain in any surface cracks in the part. Sometimes a developer is used to augment the see-ability of flaw indications.

In modern penetrant usage, it is desirable to recover as much of the penetrant as possible from test parts, rather than allow the used penetrant to be flushed down the drain. Also, it is desirable to accurately control the extent to which depletion of crack entrapments takes place during washing. These objectives are difficult to achieve when conventional procedures of parts washing are employed.

For one thing, when the penetrant is applied to test parts, and the parts are allowed to drain, the thickness of the layer of penetrant on the parts may vary considerable depending on the viscosity of the penetrant liquid, the duration of the drain time, and the orientation of surface areas. In some cases, puddles may form in horizontal or concave surfaces, or in blind holes in parts.

In the conventional water-washable process where pentrant-coated parts are washed with water, there is always an "incubation period" of washing, during which the surface layer of penetrant is stripped away to expose the surface of the test part. This incubation period may vary from a fraction of a second up to fifteen seconds or more, depending on the thickness of the penetrant layer, its solubility, its viscosity, the degree of agitation of the wash water, and other factors.

In some cases, stripping off of surface penetrant may be complete within a fraction of a second on some areas of the test parts, while adjacent areas are not stripped clean until many seconds later. Since depletion of crack entrapments begins as soon as the surface penetrant is removed, and since this depletion is often extremely rapid, it turns out that variations in the stripping-removal of surface penetrant can result in severe variations in flaw detectability from one area of the part to another.

In the conventional water-washable penetrant process, the washing operation carries off surface penetrant in the form of dissolved or emulsified material. This dissolved or emulsified penetrant is difficult to extract from the wash water, although extraction can sometimes be accomplished by the use of electrolytic emulsion breakers and activated carbon or clay filters. In any event, there is a need for improvement in methods and means for recovery of used penetrant materials.

I have discovered that it is possible to treat test parts with a special pre-wash stripper composition in such a way that surface penetrant is removed without any material depletion of entrapments in surface discontinuities. At the same time, I have found it possible, particularly with respect to preferred types of water-washable penetrants, to be hereinafter described, to recover the stripped-off penetrant for re-use.

The principal object of the invention, therefore, is to provide a pre-wash stripper composition for use with water-washable inspection penetrants which is capable of removing surface penetrant from test parts without causing any material depletion of actual crack entrapments.

Another object of the invention is to provide a pre-wash stripper composition which will remove excess surface penetrant from test parts in such a way that the stripped-off penetrant may be recovered for re-use.

Other and incidental objects of the invention will in part be obvious, and will in part become apparent from the following specification.

For the purpose of the present invention, only certain kinds of water-washable penetrants may be utilized. Such penetrants are those which are capable of forming saturated solutions in water. Penetrants which are not adaptable for the purpose of the invention, or only partly so, are those which are completely water soluble or extensively emulsifiable. For example, water-washable penetrants formulated on a glycol vehicle may exhibit an infinite solubility in water, hence they will not form saturated solutions. Likewise, some water-washable penetrants which are self-emulsifiable do not exhibit any separation by saturation in water, however some other emulsifiable penetrants will form saturated mixtures.

Preferred water-washable penetrant compositions for use in connection with the present invention are the slow-solubility penetrant composition such as are disclosed and claimed in my above-mentioned copending application Ser. Nos. 431,236, 482,465, and 513,084. These penetrants are formulated on certain low-solubility liquids which have solubilities in water in the range of .001% up to about 3%. Penetrant materials of this kind easily form saturated solutions, and it is easy to recover excess penetrant which is introduced into wash water above and beyond the saturation point. Excess penetrant carried into water which is saturated with the penetrant will simply separate by flotation into a layer of penetrant which can be skimmed off and recovered.

In the case of self-emulsifiable penetrants consisting of an oil containing detergent ingredients, I have found that if the detergent content is reduced to a few percent or less, the penetrant will still remain emulsifiable so that it may be washed from test surfaces, but it tends to become less soluble as the detergent content is reduced, and becomes capable of forming saturated mixtures which will separate by flotation.

In any event, it will be understood that the present invention involves the use of water-washable penetrant materials, regardless of their chemical nature, which are capable of forming saturated solutions.

I have discovered that an effective pre-wash stripper composition may be made simply by adding the water-washable penetrant to a volume of pre-wash water in an amount sufficient to form a saturated solution or mixture. Parts which are coated with the penetrant may be subjected to a spray of this saturated solution, with the result that surface penetrant is removed by the scrubbing action of spray droplets, but the pre-wash solution is already saturated with penetrant and cannot dissolve entrapments of penetrant. Hence, the pre-wash action can proceed only to the point where surface penetrant is completely removed, and then its action stops, that is for all practical purposes.

In cases where the stripper composition of the invention is used to remove surface penetrant for the purpose of recovery and re-use, test parts coated with the water-washable penetrant are spray-washed with a saturated solution of the penetrant and surface penetrant is stripped off by the scrubbing action of the spray droplets. Since the saturated pre-wash liquid cannot dissolve more penetrant, the penetrant which is stripped from the test parts accumulates as a floating layer on the saturated solution, and may be skimmed off and re-used.

A preferred method of using the pre-wash stripper composition of the invention is to maintain it in a reservoir tank and a re-circulating spray-wash system. A layer of undissolved penetrant is kept floating on the surface of the stripper solution in the reservoir tank so as to insure that the water is at all times saturated with dissolved penetrant. The saturated solution is drawn out of the bottom of the tank, and is pumped to a spray nozzle or system of nozzles directed against test parts being processed. Water and stripped-off penetrant which drains from the test parts is returned to the reservoir tank where excess penetrant floats to the surface and accumulates in the existing layer of penetrant.

Following treatment of penetrant-coated test parts with the pre-wash stripper composition of the invention, other appropriate steps in the penetrant process may be performed, as for example a finish-wash operation, drying, development, and inspection of the test parts.

The pre-wash stripper composition of the invention may be employed at any desired temperature, however in many cases I have found it desirable to utilize the material at an elevaated temperature, above 100° F., and preferably in the range of from 100° up to about 130° F. It will be understood that the presence of dissolved penetrant in the pre-wash stripper water solution, up to the point of saturation, acts to inhibit further solvency action of the solution on penetrant entrapments in test parts. For this reason, I have designated the compositions of the invention as "Inhibited Pre-Wash Strippers".

Although the invention has been described with reference to particular embodiments thereof, it will be understood that various changes may be made therein without departing from the spirit of the invention or the scope of the appended claim.

I claim:

1. In an inspection penetrant process in which a slow-solubility-type water-washable dyed liquid penetrant is applied to a test surface and surface penetrant is removed by washing said penetrant-treated test surface with water, the improvement consisting of a step of surface washing with a stripper composition, said step being introduced prior to finish-washing said penetrant-treated test surface, said stripper composition consisting of water saturated with dissolved slow-solubility penetrant.

2. In a water-washable inspection penetrant process employing a slow-solubility-type water-soluble dyed liquid penetrant, and in which the following steps are carried out in sequence; (1) apply the penetrant to a test part, (2) wash the test part with water to remove excess surface penetrant, leaving entrapments of penetrant in surface flaws, (3) dry the test part, and (4) inspect for the presence of entrapments of penetrant in surface flaws, the improvement in which the following step is introduced prior to the step of washing the test part with water; (1-a) spray wash the test part with water saturated with dissolved slow-solubility penetrant, whereby excess surface penetrant is stripped off and removed without simultaneous depletion of flaw entrapments of penetrant.

* * * * *